United States Patent [19]

Lindner et al.

[11] Patent Number: 5,196,562

[45] Date of Patent: Mar. 23, 1993

[54] SUBSTITUTED 1,3,5-TRIAZINETRIONES, FOR USE AGAINST PARASITIC PROTOZOA

[75] Inventors: Werner Lindner, Cologne; Axel Haberkorn, Wuppertal, both of Fed. Rep. of Germany

[73] Assignee: Bayer Aktiengesellschaft, Leverkusen, Fed. Rep. of Germany

[21] Appl. No.: 457,666

[22] Filed: Dec. 27, 1989

Related U.S. Application Data

[62] Division of Ser. No. 414,551, Sep. 28, 1989, Pat. No. 4,933,341.

[30] Foreign Application Priority Data

Oct. 8, 1988 [DE] Fed. Rep. of Germany ....... 3834272

[51] Int. Cl.$^5$ .................. C07C 255/40; C07D 513/00
[52] U.S. Cl. .................... 558/404; 548/180; 558/408; 558/410
[58] Field of Search ......................... 558/404; 548/180

[56] References Cited

PUBLICATIONS

Pissiotas, et al., C.A., 96, (1982), 96:19854k.
Chemical Abstracts Formula Index, vol. 96, 1982, p. 1518f.

Primary Examiner—Joseph Paul Brust
Attorney, Agent, or Firm—Sprung Horn Kramer & Woods

[57] ABSTRACT

Protecting against parasitic protozoa with substituted 1,3,5-triazinetriones of the formula

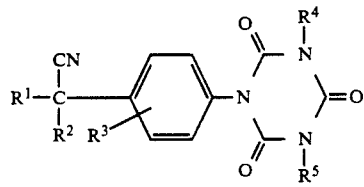

in which
R$^1$ represents aromatic or heteroaromatic radicals, each of which is optionally substituted,
R$^2$ represents H, alkyl, alkenyl, alkinyl or aralkyl, each of which is optionally substituted,
R$^3$ represents one or more identical or different radicals from the group consisting of hydrogen, halogen, alkyl, halogenoalkyl, alkoxy, alkylthio, halogenoalkoxy, halogenoalkylthio, cyano, alkoxycarbonyl, alkylsulphonyl and halogenoalkylsulphonyl,
R$^4$ represents hydrogen, a straight-chain, branched or cyclic alkyl radical, alkenyl, alkinyl, aralkyl or aryl, each of which is optionally substituted, and
R$^5$ represents hydrogen, optionally substituted alkyl, alkenyl, alkinyl or aralkyl.

Also novel intermediates therefor.

2 Claims, No Drawings

SUBSTITUTED 1,3,5-TRIAZINETRIONES, FOR USE AGAINST PARASITIC PROTOZOA

This is a division of application Ser. No. 414,551, filed Sep. 28, 1989, now U.S. Pat. No. 4,933,341 filed Jun. 12, 1990.

The present invention relates to novel substituted 1,3,5-triazinetriones, processes for their preparation, intermediates for carrying out these processes, and their use against parasitic protozoa.

The use of substituted 1,3,5-triazinetriones for controlling coccidia is known. However, the action of these compounds is not satisfactory in every case.

The present invention relates to 1. Novel substituted 1,3,5-triazinetriones of the general formula (I)

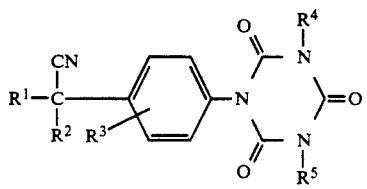

in which
R$^1$ represents aromatic or heteroaromatic radicals, each of which is optionally substituted,
R$^2$ represents H, alkyl, alkenyl, alkinyl or aralkyl, each of which is optionally substituted,
R$^3$ represents one or more identical or different radicals from the group comprising hydrogen, halogen, alkyl, halogenoalkyl, alkoxy, alkylthio, halogenoalkoxy, halogenoalkylthio, cyano, alkoxycarbonyl, alkylsulphonyl and halogenoalkylsulphonyl,
R$^4$ represents hydrogen, a straight-chain, branched or cyclic alkyl radical, alkenyl, alkinyl, aralkyl or aryl, each of which is optionally substituted, and
R$^5$ represents hydrogen, optionally substituted alkyl, alkenyl, alkinyl or aralkyl.

2. Process for the preparation of substituted 1,3,5-triazinetriones of the general formula (I)

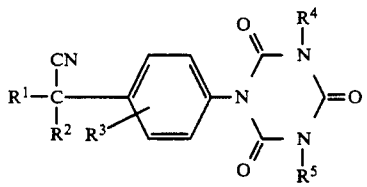

in which
R$^1$ represents aromatic or heteroaromatic radicals, each of which is optionally substituted,
R$^2$ represents hydrogen, alkyl, alkenyl, alkinyl or aralkyl, each of which is optionally substituted,
R$^3$ represents one or more identical or different radicals from the group comprising hydrogen, halogen, alkyl, halogenoalkyl, alkoxy, alkylthio, halogenoalkoxy, halogenoalkylthio, cyano, alkoxycarbonyl, alkylsulphonyl and halogenoalkylsulphonyl,
R$^4$ represents hydrogen, a straight-chain, branched or cyclic alkyl radical, alkenyl, alkinyl, aralkyl or aryl, each of which is optionally substituted, and
R$^5$ represents hydrogen, optionally substituted alkyl, alkenyl, alkinyl or aralkyl,
in which a) compounds of the formula (II)

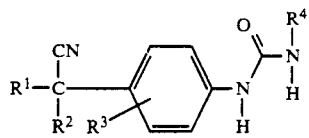

in which R$^1$, R$^2$, R$^3$ and R$^4$ have the abovementioned meanings,
are reacted with a substituted carbonyl isocyanate of the formula (III)

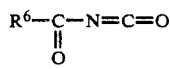

where
R$^6$ represents a halogen atom, an alkoxy group or an aryloxy group.

b) Compounds of the formula (II) are reacted with compounds of the formula (IV)

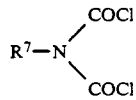

in which
R$^7$ represents hydrogen or alkyl,
if appropriate in the presence of acid acceptors.

c) Compounds of the formula (V)

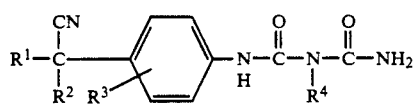

in which R$^1$, R$^2$, R$^3$ and R$^4$ have the abovementioned meanings,
are reacted with compounds of the formula (VI)

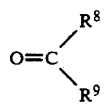

in which R$^8$, R$^9$ represent an alkoxy group, if appropriate in the presence of bases.

d) Compounds of the formula (Ia)

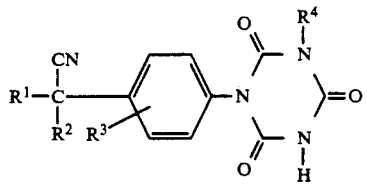

in which R$^1$, R$^2$, R$^3$ and R$^4$ have the abovementioned meanings,
are reacted with compounds of the formula (VII)

in which $R^5$ represents optionally substituted alkyl, alkenyl, alkinyl and aralkyl and A represents halogen, $OSO_2$, alkyl, $OSO_2$-aryl and $OSO_2$-halogenoalkyl.

3. Novel compounds of the formula (II)

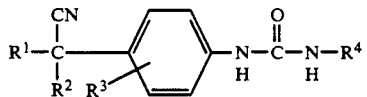

in which $R^1$, $R^2$, $R^3$ and $R^4$ have the abovementioned meanings

4. Process for the preparation of the compounds of the formula (II) in accordance with 3, characterized in that a) compounds of the formula (VIII)

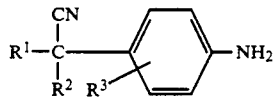

in which $R^1$, $R^2$ and $R^3$ have the abovementioned meanings, are reacted with isocyanates of the formula (IX)

in which $R^4$ has the meanings mentioned in the case of the compounds of the formula (I).

b) Compounds of the formula (X)

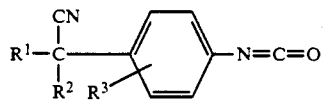

in which $R^1$, $R^2$ and $R^3$ have the meanings mentioned in the case of the compounds of the formula (I) are reached with compounds of the formula (XI)

in which $R^4$ has the abovementioned meanings.

5. Novel compounds of the formula (V)

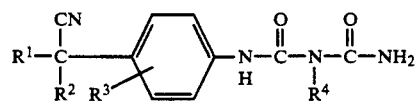

in which $R^1$, $R^2$, $R^3$ and $R^4$ have the abovementioned meanings.

6. Process for the preparation of the novel compounds of the formula (V) in accordance with 5, characterized in that compounds of the formula (II) are reacted with phosgene and ammonia.

7. Novel compounds of the formula (VIII)

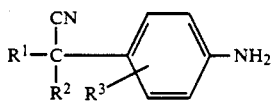

where $R^1$ represents heteroaromatic radicals with the exception of thiophene or represents phenyl substituted by halogenalkylthio or halogenalkoxy, and $R^2$ and $R^3$ have the meanings mentioned in the case of (I).

8. Process for the preparation of the novel compounds of the formula (VIII) in accordance with 7, characterized in that compounds of the formula (XII)

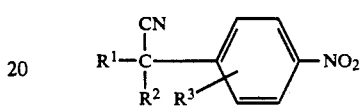

where $R^1$, $R^2$ and $R^3$ have the abovementioned meanings are hydrogenated.

9. Novel compounds of the formula (X)

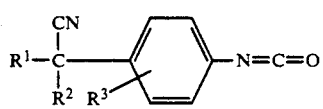

in which $R^1$, $R^2$ and $R^3$ have the meanings described in the case of 4 b).

10. Process for the preparation of the novel compounds of the formula (X) in accordance with 9, characterized in that compounds of the formula (VIII)

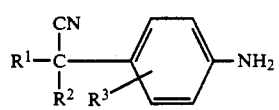

in which $R^1$, $R^2$ and $R^3$ have the meanings described in the case of 4 b), are reacted with phosgene.

11. Novel compounds of the formula (XII)

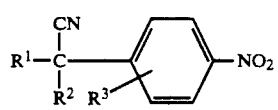

in which $R^1$, $R^2$ and $R^3$ have the meanings described in the case of 7.

12. Process for the preparation of the novel compounds of the formula (XII) in accordance with 11, characterized in that compounds of the formula (XIII)

in which $R^1$ and $R^2$ have the meanings described in the case of 7, are reacted with compounds of the formula (XIV)

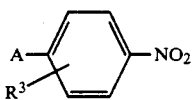

where $R^3$ has the meaning described in the case of 1, and A represents halogen.

The compounds of the formula (I) and their salts with acids or bases are outstandingly suitable for controlling parasitic protozoa.

Preferred compounds of the formula (I) are those where $R^1$ represents thiazolyl, oxazolyl, benzothiazolyl, benzoxazolyl, pyridinyl, pyrimidinyl, pyrazinyl, indolyl, benzimidazolyl, phenyl or naphthyl, each of which is optionally substituted by halogen, alkyl, cyano, nitro, O-alkyl, S-alkyl, halogenoalkyl, halogenoalkoxy, halogenoalkylthio, halogenoalkylsulphinyl or halogenoalkylsulphonyl, $R^2$ represents H or alkyl, $R^3$ represents one or more identical or different radicals from the group consisting of halogen, alkyl, halogenoalkyl, alkoxy, halogenoalkoxy, alkylthio, halogenoalkylthio or cyano, $R^4$ represents hydrogen, alkyl, alkenyl or alkinyl, each of which is optionally substituted by halogen, halogenoalkyl, alkoxy, alkylthio, aryloxy, arylthio or aryl, and $R^5$ represents hydrogen or alkyl.

Particularly preferred compounds of the formula (I) are those in which $R^1$ represents phenyl, pyridyl or benzothiazolyl each of which is substituted by one or more identical or different radicals from the group consisting of halogen, $C_{1-4}$-alkyl, $C_{1-4}$-halogenoalkyl, $C_{1-4}$-alkoxy, $C_{1-4}$-alkylthio, $C_{1-4}$-halogenoalkoxy, $C_{1-4}$-halogenoalkylthio, cyano, $C_{1-4}$-alkoxycarbonyl, $C_{1-4}$-alkylsulphinyl, $C_{1-4}$-alkylsulphonyl, $C_{1-4}$-halogenoalkylsulphinyl and $C_{1-4}$-halogenoalkylsulphonyl, $R^2$ represents H or $C_{1-4}$-alkyl, $R^3$ represents one or more identical or different radicals from the group consisting of hydrogen, halogen, $C_{1-4}$-alkyl and $C_{1-4}$-halogenoalkyl, $R^4$ represents hydrogen or $C_{1-4}$-alkyl and $R^5$ represents hydrogen or $C_{1-4}$-alkyl.

Very particularly preferred compounds of the formula (I) are those in which $R^1$ represents phenyl which is optionally substituted by halogen, in particular chlorine, bromine or fluorine, or by $C_{1-4}$-halogenoalkyl, in particular trifluoromethyl, or by $C_{1-4}$-halogenoalkylthio in particular trifluoromethylthio, or by $C_{1-4}$-halogenoalkylsulphinyl, in particular trifluoromethylsulphonyl, $C_{1-4}$-halogenalkylsulphonyl, in particular trifluoromethylsulphonyl, $C_{1-4}$-halogenoalkoxy, in particular trifluoromethoxy, or by $C_{1-4}$-alkyl, in particular methyl, $R^2$ represents H or $C_{1-4}$-alkyl, in particular methyl, $R^3$ represents halogen, in particular bromine, chlorine or fluorine, or $C_{1-4}$-alkyl, in particular methyl, or halogenoalkyl, in particular trifluoromethyl, $R^4$ represents $C_{1-4}$-alkyl, in particular methyl, and $R^5$ represents hydrogen.

Individual compounds which may be mentioned are:

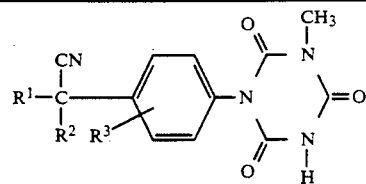

| $R^1$ | $R^2$ | $R^3$ |
|---|---|---|
| 4-Cl-Phenyl | H | 3,5 Cl |
| 4-SCF$_3$-Phenyl | H | 3,5 Cl |
| 4-OCF$_3$-Phenyl | H | 3,5 Cl |
| 4-SOCF$_3$-Phenyl | H | 3,5 Cl |
| 4-SO$_2$ CF$_3$-Phenyl | H | 3,5 Cl |
| 4-CF$_3$-Phenyl | H | 3,5 Cl |
| 3-Cl-4CF$_3$-Phenyl | H | 3,5 Cl |
| 3,4-Cl$_2$-Phenyl | H | 3,5 Cl |

The compounds which follow may furthermore be mentioned:

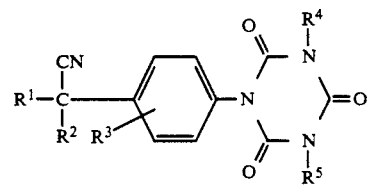

| $R^1$ | $R^2$ | $R^3$ | $R^4$ | $R^5$ |
|---|---|---|---|---|
| 2-Benzthiazolyl | H | 3-Cl | CH$_3$ | H |
| 2-(6-Cl-Benzothiazolyl) | H | 3-Cl | CH$_3$ | H |
| 2-(5,6-Cl-Benzothiazolyl) | H | 3-Cl | CH$_3$ | H |
| 2-Benzoxazolyl | H | 3-Cl | CH$_3$ | H |
| 2-Pyridinyl | H | 3-Cl | CH$_3$ | H |
| 3-Pyridinyl | | | | |
| 4-Cl-Phenyl | H | 3-CH$_3$ | CH$_3$ | H |
| 4-Cl-Phenyl | H | 3,5-(CH$_3$)$_2$ | CH$_3$ | H |
| 4-Cl-Phenyl | H | 3-Cl | CH$_3$ | H |
| 4-Cl-Phenyl | H | 3-Cl,5-CH$_3$ | CH$_3$ | H |
| 4-Cl-Phenyl | H | 3,5-Br$_2$ | CH$_3$ | H |
| 4-Cl-Phenyl | H | 3-CF$_3$ | CH$_3$ | H |
| 4-Cl-Phenyl | H | 3,5-Cl | C$_2$H$_5$ | H |
| 4-Cl-Phenyl | H | 3-CH$_3$ | —C$_2$H$_5$ | H |
| 4-CF$_3$-Phenyl | H | 3-CH$_3$ | CH$_3$ | H |
| 4-CF$_3$-Phenyl | H | 3,5-(CH$_3$)$_2$ | CH$_3$ | H |
| 4-CF$_3$-Phenyl | H | 3-Cl | CH$_3$ | H |
| 4-CF$_3$-Phenyl | H | 3-Cl,5-CH$_3$ | CH$_3$ | H |
| 4-CF$_3$-Phenyl | H | 3-5-Br$_2$ | CH$_3$ | H |
| 4-CF$_3$-Phenyl | H | 3-CF$_3$ | CH$_3$ | H |
| 4-CF$_3$-Phenyl | H | 3,5-Cl$_2$ | C$_2$H$_5$ | H |
| 4-CF$_3$-Phenyl | H | 3-CH$_3$ | C$_2$H$_5$ | H |
| 3,4-Cl$_2$-Phenyl | H | 3-CH$_3$ | CH$_3$ | H |
| 3,4-Cl$_2$-Phenyl | H | 3-Cl | CH$_3$ | H |
| 3,4-Cl$_2$-Phenyl | H | 3-Cl,5-CH$_3$ | CH$_3$ | H |
| 3,4-Cl$_2$-Phenyl | H | 3,5-Br$_2$ | CH$_3$ | H |
| 3,4-Cl$_2$-Phenyl | H | 3-CF$_3$ | CH$_3$ | H |
| 3,4-Cl$_2$-Phenyl | H | 3,5-Cl$_2$ | C$_2$H$_5$ | H |
| 3,4-Cl$_2$-Phenyl | H | 3-CH$_3$ | C$_2$H$_5$ | H |
| 2,4-Cl$_2$-Phenyl | H | 3-CH$_3$ | CH$_3$ | H |
| 2,4-Cl$_2$-Phenyl | H | 3-Cl | Ch$_3$ | H |
| 2,4-Cl$_2$-Phenyl | H | 3-Cl,5-CH$_3$ | CH$_3$ | H |
| 2,4-Cl$_2$-Phenyl | H | 3,5-Br$_2$ | CH$_3$ | H |
| 2,4-Cl$_2$-Phenyl | H | 3-CF$_3$ | CH$_3$ | H |
| 2,4-Cl$_2$-Phenyl | H | 3,5-Cl$_2$ | C$_2$H$_5$ | H |
| 2,4-Cl$_2$-Phenyl | H | 3-CH$_3$ | C$_2$H$_5$ | H |
| 3-Cl-Phenyl | H | 3-CH$_3$ | CH$_3$ | H |
| 3-Cl-Phenyl | H | 3-Cl | CH$_3$ | H |
| 3-Cl-Phenyl | H | 3-Cl,5-CH$_3$ | CH$_3$ | H |
| 3-Cl-Phenyl | H | 3,5-Br$_2$ | CH$_3$ | H |
| 3-Cl-Phenyl | H | 3-CF$_3$ | CH$_3$ | H |
| 3-Cl-Phenyl | H | 3,5-Cl$_2$ | C$_2$H$_5$ | H |
| 3-Cl-phenyl | H | 3-CH$_3$ | C$_2$H$_5$ | H |

-continued

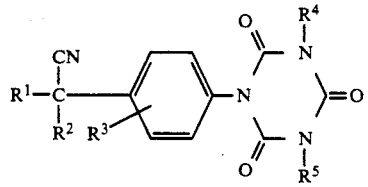

| R$^1$ | R$^2$ | R$^3$ | R$^4$ | R$^5$ |
|---|---|---|---|---|
| 4-SCF$_3$-Phenyl | H | 3-CH$_3$ | CH$_3$ | H |
| 4-SCF$_3$-Phenyl | H | 3,5-(CH$_3$)$_2$ | CH$_3$ | H |
| 4-SCF$_3$-Phenyl | H | 3-Cl | CH$_3$ | H |
| 4-SCF$_3$-Phenyl | H | 3-Cl,5-CH$_3$ | CH$_3$ | H |
| 4-SCF$_3$-Phenyl | H | 3,5-Br$_2$ | CH$_3$ | H |
| 4-SCF$_3$-Phenyl | H | 3-CF$_3$ | CH$_3$ | H |
| 4-SCF$_3$-Phenyl | H | 3,5-Cl$_2$ | C$_2$H$_5$ | H |
| 4-SCF$_3$-Phenyl | H | 3,5-Cl$_2$ | C$_2$H$_5$ | CH$_3$ |
| 4-SCF$_3$-Phenyl | H | 3,5-Cl$_2$ | CH$_3$ | CH$_3$ |
| 4-SCF$_3$-Phenyl | H | 3-CH$_3$ | CH$_3$ | H |
| 4-OCF$_3$-Phenyl | H | 3-CH$_3$ | CH$_3$ | H |
| 4-OCF$_3$-Phenyl | H | 3,5-(CH$_3$)$_2$ | CH$_3$ | H |
| 4-SCF$_3$-Phenyl | CH$_3$ | 3,5-Cl$_2$ | CH$_3$ | H |
| 4-OCF$_3$-Phenyl | CH$_3$ | 3,5-Cl$_2$ | CH$_3$ | H |
| 4-OCF$_3$-Phenyl | H | 3-Cl | CH$_3$ | H |
| 4-OCF$_3$-Phenyl | H | 3-Cl,5-CH$_3$ | CH$_3$ | H |
| 4-OCF$_3$-Phenyl | H | 3,5-Br$_2$ | CH$_3$ | H |
| 4-OCF$_3$-Phenyl | H | 3-CF$_3$ | CH$_3$ | H |
| 4-OCF$_3$-Phenyl | H | 3,5-Cl$_2$ | C$_2$H$_5$ | H |
| 4-OCF$_3$-Phenyl | H | 3-Cl | C$_2$H$_5$ | H |
| 4-CN-Phenyl | H | 3-CH$_3$ | CH$_3$ | H |
| 4-CN-Phenyl | H | 3-Cl | CH$_3$ | H |
| 4-CN-Phenyl | H | 3-Cl,5-CH$_3$ | CH$_3$ | H |
| 4-CN-Phenyl | H | 3,5-Br$_2$ | CH$_3$ | H |
| 4-CN-Phenyl | H | 3-CF$_3$ | CH$_3$ | H |
| 4-CN-Phenyl | H | 3,5-Cl$_2$ | C$_2$H$_5$ | H |
| 4-CN-Phenyl | H | 3-Cl | C$_2$H$_5$ | H |
| 3-OCH$_3$-Phenyl | H | 3-CH$_3$ | CH$_3$ | H |
| 4-OCH$_3$-Phenyl | H | 3-Cl | CH$_3$ | H |
| 4-OCH$_3$-Phenyl | H | 3-Cl,5-CH$_3$ | CH$_3$ | H |
| 4-OCH$_3$-Phenyl | H | 3,5-Br$_2$ | CH$_3$ | H |
| 4-OCH$_3$-Phenyl | H | 3-CF$_3$ | CH$_3$ | H |
| 4-OCH$_3$-Phenyl | H | 3,5-Cl$_2$ | C$_2$H$_5$ | H |
| 4-OCH$_3$-Phenyl | H | 3-Cl | C$_2$H$_5$ | H |
| 4-SO$_2$CF$_3$-Phenyl | H | 3-CH$_3$ | CH$_3$ | H |
| 4-SO$_2$CF$_3$-Phenyl | H | 3,5-(CH$_3$)$_2$ | CH$_3$ | H |
| 4-SO$_2$CF$_3$-Phenyl | H | 3-Cl | CH$_3$ | H |
| 4-SO$_2$CF$_3$-Phenyl | H | 3-Cl,5-CH$_3$ | CH$_3$ | H |
| 4-SO$_2$CF$_3$-Phenyl | H | 3,5-Br$_2$ | CH$_3$ | H |
| 4-SO$_2$CF$_3$-Phenyl | H | 3-CF$_3$ | CH$_3$ | H |
| 4-SO$_2$CF$_3$-Phenyl | H | 3,5-Cl$_2$ | C$_2$H$_5$ | H |
| 4-SO$_2$CF$_3$-Phenyl | H | 3-Cl | C$_2$H$_5$ | H |
| 4-SOCF$_3$-Phenyl | H | 3-CH$_3$ | CH$_3$ | H |
| 4-SOCF$_3$-Phenyl | H | 3-Cl | CH$_3$ | H |
| 4-SOCF$_3$-Phenyl | H | 3-Cl,5-CH$_3$ | CH$_3$ | H |
| 4-SOCF$_3$-Phenyl | H | 3,5-Br$_2$ | CH$_3$ | H |
| 4-SOCF$_3$-Phenyl | H | 3-CF$_3$ | CH$_3$ | H |
| 4-SOCF$_3$-Phenyl | H | 3,5-Cl$_2$ | C$_2$H$_5$ | H |
| 4-SOCF$_3$-Phenyl | H | 3-Cl | C$_2$H$_5$ | H |
| 2-Benzimidazolyl | H | 3-Cl | CH$_3$ | H |
| 2-Indolyl | H | 3-Cl | CH$_3$ | H |

If, in process 2 a, 2,6-dichloro-α-(4-trifluoromethylthiophenyl)-4-methylureido-phenylacetonitrile is employed as compound II and chlorocarbonyl isocyanate as compound of the formula (III), the process may be described by the following equation:

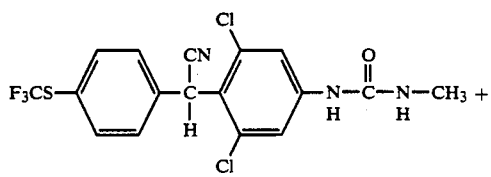

-continued

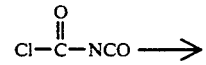

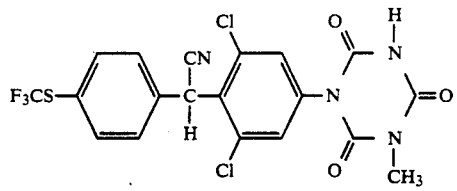

Compounds of the formula (II) are novel. Compounds of the formula (II) where R$^2$ and R$^3$ have the meanings indicated in the case of the compounds of the formula (I) as being preferred, may preferably be mentioned.

Compounds of the formula (II) which may be mentioned individually are the following.

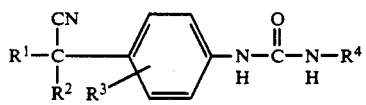

| R$^1$ | R$^2$ | R$^3$ | R$^4$ |
|---|---|---|---|
| 4-Cl-Phenyl | H | 3,5-Cl$_2$ | CH$_3$ |
| 4-OCF$_3$-Phenyl | H | 3,5-Cl$_2$ | CH$_3$ |
| 4-SOCF$_3$-Phenyl | H | 3,5-Cl$_2$ | CH$_3$ |
| 4-SO$_2$CF$_3$-Phenyl | H | 3,5-Cl$_2$ | CH$_3$ |
| 4-CH$_3$-Phenyl | H | 3,5-Cl$_2$ | CH$_3$ |
| 3,4-Cl-Phenyl | H | 3,5-Cl$_2$ | CH$_3$ |
| 4-F$_3$CO-Phenyl | H | 3-Cl | CH$_3$ |
| 4-CF$_3$-Phenyl | H | 3-CH$_3$ | CH$_3$ |
| 4-Cl-Phenyl | H | 3-Cl | CH$_3$ |
| 4-Cl-Phenyl | H | 3-CH$_3$ | CH$_3$ |

The substituted carbonyl isocyanates f the formula (III) are known.

The reaction is preferably carried out using diluents.

Suitable diluents in this process are virtually all inert organic solvents. These preferably include aliphatic and aromatic, optionally halogenated hydrocarbons, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, dimethylacetamide and N-methyl-pyrrolidone, and also dimethyl sulphoxide, tetramethylene sulphone and hexamethylphosphoric triamide.

The reaction is carried out at temperatures between 20° and 150° C., preferably between 50° and 120° C.

The process is carried out by combining and heating equimolar amounts of the compounds of the formula (II) and (III) in one of the diluents mentioned. When the reaction is complete, the mixture is cooled and the precipitated solid is filtered off, washed and dried.

If, in process 2 b for the preparation of the compounds of the formula (I), 2,6-dichloro-α-(4-trifluoromethylthiophenyl)-4-methylureido-phenylacetonitrile is employed as the compound of the formula (II) and bischlorocarbonylmethylamine as the compound of the formula (IV), the process may be described by the following diagram:

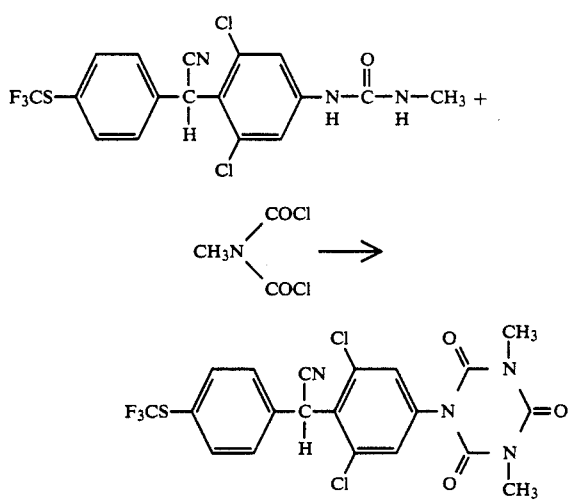

The compounds of the formula (IV) are known.

The process is carried out as described in the case of 2 a. The diluents which are used are those described in process 2 a.

If, in process 2 c, 2,6-dichloro-α-(4-trifluoromethylthiophenyl)-4-methyl-bisdiureido-phenylacetonitrile is employed as the compound of the formula (V) and diethyl carbonate as the compound of the formula (VI), the process may be described by the following diagram:

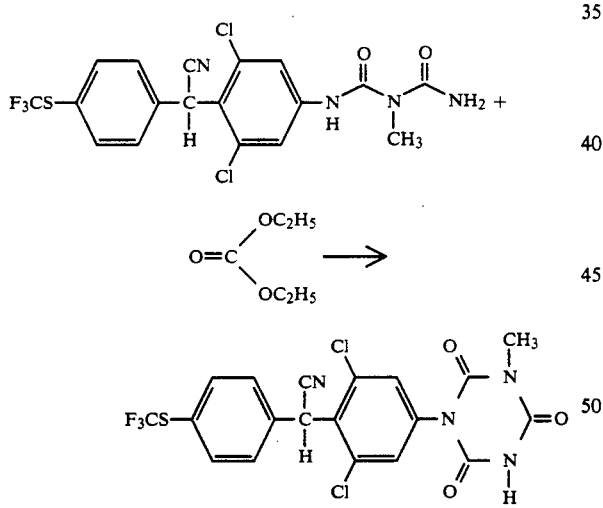

The compounds of the formula (V) are novel. Compounds of the formula (V) which may be mentioned individually are the following:

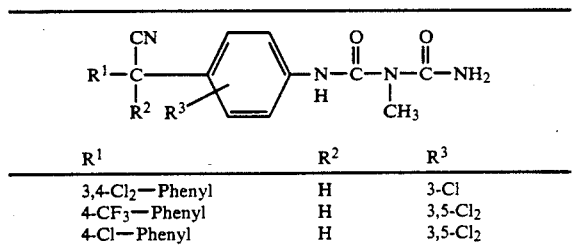

| R$^1$ | R$^2$ | R$^3$ |
|---|---|---|
| 3,4-Cl$_2$—Phenyl | H | 3-Cl |
| 4-CF$_3$—Phenyl | H | 3,5-Cl$_2$ |
| 4-Cl—Phenyl | H | 3,5-Cl$_2$ |

-continued

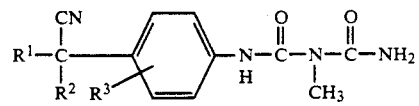

| R$^1$ | R$^2$ | R$^3$ |
|---|---|---|
| 4-OCF$_3$—Phenyl | H | 3,5-Cl$_2$ |
| 4-SCF$_3$—Phenyl | H | 3-CH$_3$ |

The process is carried out in the presence of bases. The alkali metal hydroxides, such as sodium hydroxide, alkali metal alkoxides, such as sodium ethoxide, or organic bases, such as 1,8-diazabicyclo-[5,4,0]-undec-7-ene (DBU), may be mentioned as preferred bases.

The process is carried out at temperatures between 10° and 80° C., preferably between 20° and 50° C., under atmospheric pressure or increased pressure. It is preferably carried out under atmospheric pressure. The process can be carried out using the reactants as such or in the presence of a diluent. Diluents which can be employed are all inert organic solvents which are also used when process 2 a is carried out.

The reaction is carried out by stirring a compound of the formula (V) with a compound of the formula (VI) in the presence of a base at the reaction temperature indicated. The amount of the compound of the formula If, in the process of the formula 2 d, 2,6-dichloro-α-(4-chlorophenyl)-α-methyl-4-(3-N-methyl-1,3,5-triazine- 2,4,6-(1H,3H,5H)-trione-phenylacetonitrile is employed as the compound of the formula (Ia) and methyl iodide as the compound of the formula (VII), the process may be described by the following diagram:

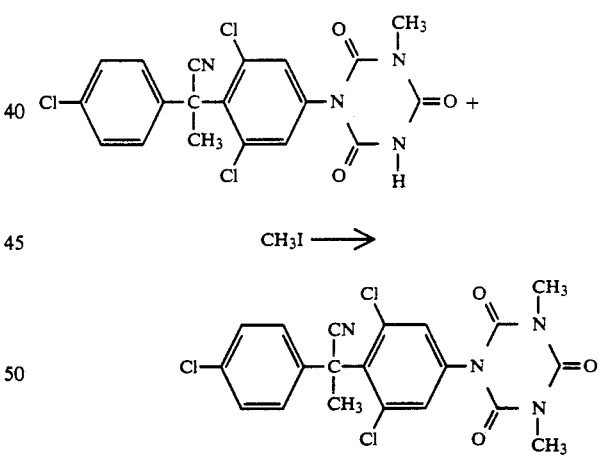

The compounds of the formula (Ia) are novel and are prepared as described in processes 2 a–c.

The compounds of the formula (IV) are known or may be prepared by methods which are known per se. In particular, methyl iodide and ethyl bromide may be mentioned.

The process is carried out by reacting a compound of the formula (Ia) in the presence of a base and of a diluent with compounds of the formula (IV). Diluents which can be employed are all inert organic solvents which also serve for carrying out process 2 a.

The process is carried out in the presence of bases. Preferred bases which may be mentioned are: alkali metal hydroxides, such as sodium hydroxide, alkali metal alkoxides, such as sodium methoxide or potassium butoxide, metal hydrides, such as sodium hydride, or organic bases, such as 1,8-diazabicyclo-[5,40]-undec-7-ene (DBU).

The process is carried out under atmospheric pressure and at temperatures between 20° and 140° C.

The reaction is carried out by combining equimolar amounts of the compound of the formula (Ia) and base, adding an equimolar amount of the compound of the formula (IV) to this mixture, and heating the reaction mixture to the reaction temperature.

If, in process 4 a for the preparation of the compounds of the formula (II), 4-amino-2,6-dichloro-α-(4-trifluoromethylthiophenyl)-phenylacetonitrile is employed as the compound of the formula (VIII) and methyl isocyanate as the compound of the formula (IX), the process may be described by the following diagram:

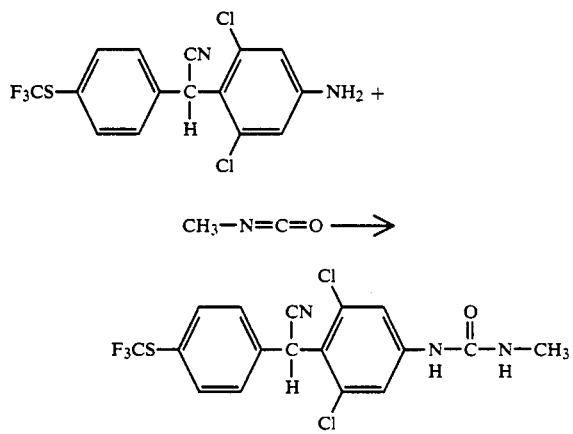

Some of the compounds of the formula (VIII) are known. The compounds of the formula (IX) are known. Novel individual compounds of the formula (VIII) which may be mentioned are:

| $R^1$ | $R^2$ | $R^3$ |
|---|---|---|
| 2-(6-Chlorobenzothiazolyl) | H | 3,5-$Cl_2$ |
| 2-Benzothiazolyl | H | 3-Cl |
| 2-Benzothiazolyl | H | 3-$CH_3$ |
| 2-Benzothiazolyl | H | 3,5-$Cl_2$ |
| 2-Benzothiazolyl | H | 3-Cl |
| 2-Indolyl | H | 3-Cl |
| 2-Pyridinyl | H | 3-Cl |
| 3-Pyridinyl | H | 3-Cl |
| 4-$SCF_3$—Phenyl | H | 3,5-Cl |
| 4-$SCF_3$—Phenyl | H | 3-Cl |
| 4-$OCF_3$—Phenyl | H | 3,5-$Cl_2$ |
| 4-$OCF_3$—Phenyl | H | 3-Cl |

The process is carried out by reacting a compound of the formula (VIII) with a compound of the formula (IX) in an inert solvent. Solvents which can be employed are all inert organic solvents which also serve for carrying out process 1 a. Pyridine may additionally be mentioned. The process is preferably carried out under atmospheric or increased pressure, preferably under atmospheric pressure and at temperatures between 20° and 120° C.

The reaction is carried out by heating a compound of the formula (VIII) with the equimolar amount or, if appropriate, in an excess, of the compound of the formula (IX) in a solvent.

If, in process 4 b for the preparation of the compounds of the formula (II), If, in process 4-isocyanato-2,6-dichloro-α-(4-trifluoromethylthiophenyl)-phenylacetonitrile is employed as the compound of the formula (X) and propylamine as the compound of the formula (XI), the process may be described by the following equation:

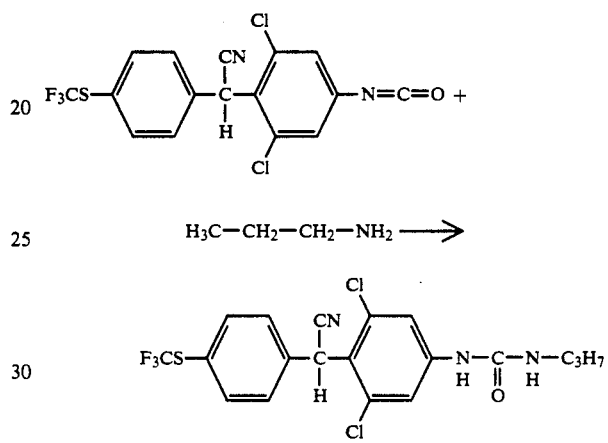

Individual compounds of the formula (X) which may be mentioned are:

| $R^1$ | $R^2$ | $R^3$ |
|---|---|---|
| Benzothiazolyl | H | 3,5-$Cl_2$ |
| 4-Cl—Phenyl | H | 3-Cl |
| 4-Cl—Phenyl | H | 3,5-$Cl_2$ |
| 4-$OCF_3$—Phenyl | H | 3-$CH_3$ |
| 4-$OCF_3$—Phenyl | H | 3,5-$Cl_2$ |

The process is carried out by heating a compound of the formula (X) and a compound of the formula (XI), if appropriate in the presence of a diluent. Diluents which can be used are the solvents mentioned in the preparation of the compounds (I). Pyridine may additionally be mentioned.

The reaction is carried out under atmospheric or increased pressure at temperatures between 50° and 150° C., preferably between 70° and 110° C.

The compounds are employed in equimolar ratios and the product which is obtained as a solid when the reaction is complete is filtered off.

If, in process 6 for the preparation of the compounds of the formula (V), 2,6-dichloro-α-(4-chlorophenyl)-4-methylureido-phenylacetonitrile is employed as the compound of the formula (II), the process may be described by the following equation:

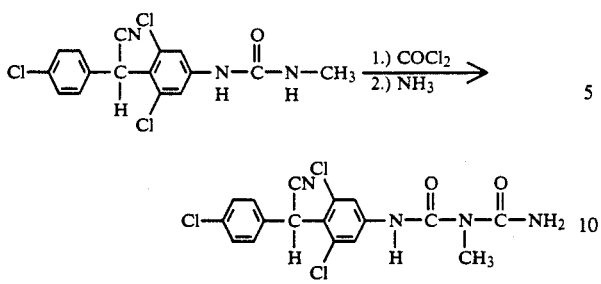

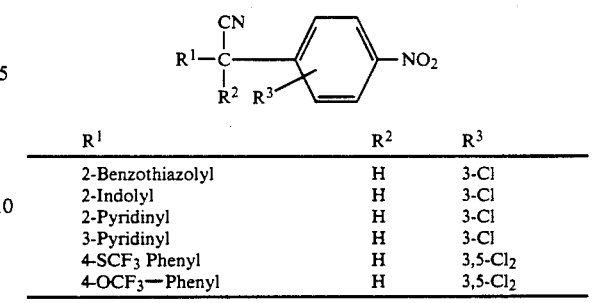

| R¹ | R² | R³ |
|---|---|---|
| 2-Benzothiazolyl | H | 3-Cl |
| 2-Indolyl | H | 3-Cl |
| 2-Pyridinyl | H | 3-Cl |
| 3-Pyridinyl | H | 3-Cl |
| 4-SCF₃ Phenyl | H | 3,5-Cl₂ |
| 4-OCF₃—Phenyl | H | 3,5-Cl₂ |

The process is carried out by reacting a urea of the formula (II), if appropriate in the presence of solvents, initially with phosgene and reacting the resulting reaction mixture with ammonia to give the compound of the formula (V).

Solvents which are used are those mentioned in the preparation of the compounds of the formula (I).

Phosgene can be added to the compound of the formula (II) in the form of a gas or in solution, in equimolar to twice the molar amount. In the form of a gas, ammonia is passed through the reaction mixture until the reaction is complete. The process is carried out at temperatures between 10° and 80° C., preferably between 20° and 60° C. When the reaction has ended, the batch is cooled and the product which has precipitated is filtered off.

Processes 4 a and 6 for the preparation of the compounds of the formula (V) can also be carried out advantageously using the "one-pot process".

If, in process 8 for the preparation of the novel compounds of the formula (VIII), 4-nitro-2,6-dichloro-α-(2-benzothiazolyl)-phenylacetonitrile is employed as the compound of the formula (XII), the process may be described by the following equation:

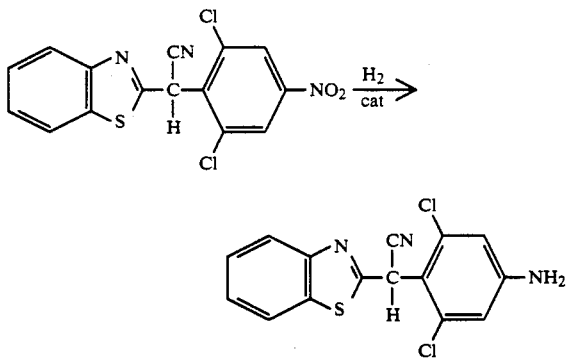

The compounds of the formula (XII) are novel under the condition that R¹ does not represent thiophene.

Novel individual compounds of the formula (XII) which may be mentioned are:

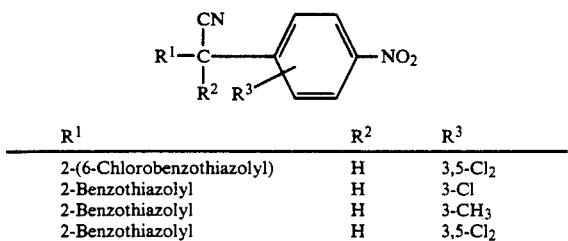

| R¹ | R² | R³ |
|---|---|---|
| 2-(6-Chlorobenzothiazolyl) | H | 3,5-Cl₂ |
| 2-Benzothiazolyl | H | 3-Cl |
| 2-Benzothiazolyl | H | 3-CH₃ |
| 2-Benzothiazolyl | H | 3,5-Cl₂ |

The process is carried out by hydrogenating a compound of the formula (XII) in the presence of a noble-metal catalyst. If appropriate, the hydrogenation is carried out in the presence of a diluent under atmospheric or increased pressure.

Solvents which can preferably be used are hydrocarbons, alcohols, such as ethanol, and ethers, such as tetrahydrofuran. Catalysts which can be used are platinum, palladium, ruthenium, thodium and, preferably, platinum. The process is carried out at temperatures between 20° and 130° C. preferably between 20° and 50° C. The catalysts are employed in a ratio of 0.01% to 5%.

If, in process 10 for the preparation of the novel compounds of the formula (X), 2,6-dichloro-α-(2-benzothiazolyl)-4-amino-phenylacetonitrile is employed, the process may be described by the following diagram:

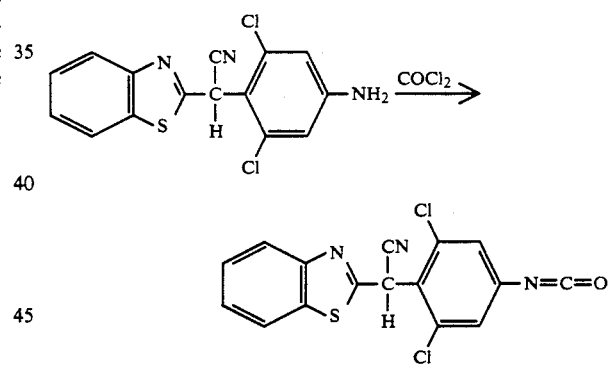

The amines of the formula (VIII) can be reacted with phosgene with or without solvents.

Diluents which may be mentioned in particular are aliphatic and aromatic, optionally halogenated hydrocarbons, such as pentane, hexane, heptanecyclohexane, petroleum ether, benzine, ligroin, benzene, toluene, methyl chloride, ethylene chloride, chloroform, carbon tetrachloride, chlorobenzene and o-dichlorobenzene.

The reaction is carried out at −20°−+80° C., preferably at −10°−+100° C. It can be carried out under atmospheric pressure or under increased pressure.

The starting substances are employed in equimolar amounts, an excess of phosgene of 2-3 moles per mole of amine of the formula (VIII) is preferred.

The reaction is carried out in the absence or presence of acid-binding agents. Examples of preferred acid-binding agents are tertiary amines, such as pyridine, or dimethylamine.

The amines of the formula (VIII) are added to a solution of phosgene and reacted, if appropriate, with passing in more phosgene. The reaction can also be carried out without solvents.

If, in process 12 for the preparation of the compounds of the formula (XII), 2-benzothiazolylacetonitrile is employed as the compound of the formula (XIII) and 3,4,5-trichloronitrobenzene as the compound of the formula (XIV), the process may be described by the following diagram:

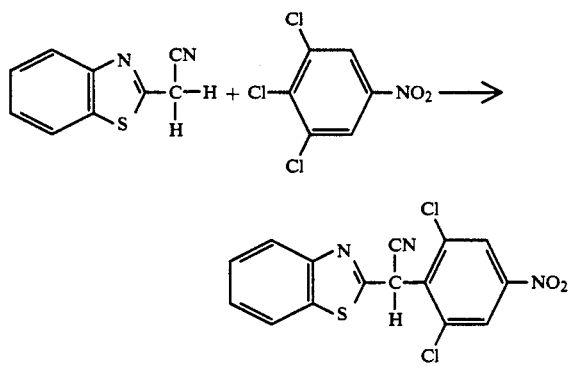

The compounds of the formula (XII) and (XIII) are known or can be prepared in analogy to known processes.

The process is carried out by reacting a compound of the formula (XIII) with compounds of the formula (XIV), if appropriate in the presence of a diluent.

Suitable diluents in this process are virtually all inert organic solvents. These preferably include aliphatic and aromatic, optionally halogenated hydrocarbons, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

The reaction is carried out in the presence of inorganic or organic acid acceptors.

Examples of acid acceptors which may be mentioned are:

Alkali metal hydroxides, such as, for example, sodium hydroxide and potassium hydroxide, alkaline earth metal hydroxides, such as, for example, calcium hydroxide, alkali metal carbonates and alkali metal alkoxides, such as sodium carbonate, potassium carbonate, sodium methoxide, potassium methoxide, sodium ethoxide or potassium ethoxide, metal hydrides, such as sodium hydride, furthermore aliphatic, aromatic or heterocyclic amines, for example triethylamine, pyridine, 1,5-diazabiccylo-[4,3,0]-non-5-ene (DBN), 1,8-diazabicyclo-[5,4,0]-undec-7-ene (DBU) and 1,4-diazabicyclo-[2,2,2]-octane (DABCO).

Catalysts which can be employed are crown ethers, such as 18-crown-6, or quaternary ammonium compounds, such as benzyltriethylammonium chloride.

The reaction is carried out at temperatures between 50 and 200° C., preferably between 80 and 160° C., under atmospheric pressure or increased pressure.

The process is carried out by combining equimolar amounts of the compounds of the formula II and III in one of the solvents indicated, and heating the mixture. When the reaction is complete, the reaction mixture is acidified using dilute inorganic acid (for example hydrochloric acid), and the resulting precipitate is filtered off, washed and dried.

The active compounds are suitable for controlling parasitic protozoa which occur and in animal keeping and livestock breeding in livestock, breeding stock, animals in zoos, laboratory animals, experimental animals and pets, while having a favorable toxicity towards warmblooded animals. In this context, they are active against all or individual developmental stages cf the pests as well as against resistant and normally-sensitive strains. Control of the parasitic protozoa is intended to reduce disease, deaths and lower performance (for example in the production of meat, milk, wool, skins, eggs, honey, etc.), so that application of the active compounds makes it possible that animal keeping is more economical and simpler.

The parasitic protozoa include:

Mastigophora (Flagellata), such as, for example, Trypanosomatidae, for example Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica, such as, for example, Trichomonadidae, for example Giardia lamblia, G. canis.

Sarcomastigophora (Rhizopoda), such as Entamoebidae, for example Entamoeba histolytica, Hartmanellidae, for example Acanthamoeba sp., Hartmanella sp.

Apicomplexa (Sporozoa), such as Eimeridae, for example Eimeria acervulina, E. adenoides, E. alabahmensis, E. anatis, E. anseris, E. arloingi, E. ashata, E. auburnensis, E. bovis, E. brunetti, E. canis, E. chinchillae, E. clupearum, E. columbae, E. contorta, E. crandalis, E. dabliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. pirifcrmis, E. praecox, E. residua, E. scabra, E. spec., E. stiedai, E. suis, E. tenella, E. truncata, E. truttae, E. zuernii, Globidium spec., Isospora belli, I. canis, I. felis, I. ohioensis, I. rivolta, I. spec., I. suis, Cystisospora spec., Cryptosporidium spec., such as Toxoplasmadidae, for example, Toxoplasma gondii, such as Sarcocystidae, for example, Sarcocystis bovicanis, S. bovihominis, S. ovicanis, S. ovifelis, S. spec., S. suihominis, such as Leucozoidae, for example, Leucozytozoon simondi, such as Plasmodiidae, for example, Plasmodium berghei, P. falciparum, P. malariae, P. ovale, P. vivax, P. spec., as Piroplasmea, for example, Babesia argentina, B. bovis, B. canis, B. spec., Theileria parva, Theileria spec., such as Adeleina, for example, Hepatozoon canis, H. spec.

Furthermore Myxospora and Microspora, for example Glugea spec. Nosema spec.

Furthermore Pneumocystis carinii, as well as Ciliophora (Ciliata), such as, for example, Balantidium coli, Ichthiophthirius spec., Trichodina spec., Epistylis spec.

Moreover, the compounds according to the invention are active against various fish parasites belonging to the Helminthes (worms).

Livestock and breeding stock include mammals, such as, for example, cattle, horses, sheep, pigs, goats, camels, water buffalo, donkeys, rabbits, fallow deer and reindeer, fur-bearing animals, such as, for example, minks, chinchillas and racoons, birds, such as, for example, chickens, geese, turkeys, ducks, pigeons and bird species which are intended to be kept as pets or in zoos. The animals further include economically useful fish and decorative fish.

The laboratory and experimental animals include mice, rats, guinea pigs, hamsters, dogs and cats.

The pets include cats and dogs.

The fish include economically useful fish, cultured fish, aquarium fish and decorative fish of all ages which live in fresh water and sea water. The economically useful fish and cultured fish include, for example, carp, eel, trout, whitefish, salmon, bream, roach, rudd, dobule, sole, plaice, halibut, Japanese yellowtail (Seriola quinqueradiata), Japanese eel (Anguilla japonica), red sea bream (Pagurus major), sea bass (Dicentrarchus labrax), grey mullet (Mugilus cephalus), pompano, gilthread sea bream (Sparus auratus), Tilapia spp., Chichlidae species, such as, for example, Plagioscion, Channel catfish. The agents according to the invention are particularly suitable for treating fish fry, for example carp of body length 2–4 cm. The agents are also very suitable for eel fattening.

The treatment can be carried out prophylactically or therapeutically.

The active compounds are administered directly or, in the form of suitable preparations, enterally, parenterally, dermally or nasally.

Enteral administration of the active compounds is carried out, for example, orally in the form of powders, suppositories, tablets, capsules, pastes, drinks, granules, drenches, boli, medicated feed or drinking water. Dermal administration is carried out, for example, in the form of dipping, spraying, bathing, washing, pouring-on and spotting-on, and powdering. Parenteral administration is carried out, for example, in the form of injection (intra-muscular, subcutaneous, intravenous, intraperitoneal) or by implants.

Suitable preparations are:
solutions, such as injection solutions, oral solutions, concentrates for oral administration after dilution, solutions for use on the skin or in body cavities, pour-on formulations, gels;
emulsions and suspension for oral or dermal administration as well as for injection; semi-solid preparations;
formulations in which the active compound is processed in an ointment basis or in an oil-in-water or water-in-oil emulsion basis;
solid preparations, such as powders, pre-mixes or concentrates, granules, pellets, tablets, boli, capsules; aerosols and inhalants, shaped articles containing active compound.

Injection solutions are administered intravenously, intramuscularly and subcutaneously.

Injection solutions are prepared by dissolving the active compound in a suitable solvent and, if appropriate, adding additives, such as solubilizers, acids, bases, buffer salts, antioxidants or preservatives. The solutions are sterile-filtered and drawn off.

Solvents which may be mentioned are: physiologically tolerable solvents, such as water, alcohols, such as ethanol, butanol, benzyl alcohol, glycerol, hydrocarbons, propylene glycol, polyethylene glycols, N-methyl-pyrrolidone, as well as mixtures thereof.

Where required, the active compounds may also be dissolved in physiologically tolerable vegetable or synthetic oils which are suitable for injection.

Solubilizers which may be mentioned are: solvents which facilitate the dissolution of the active compound in the main solvent or which inhibit its precipitation. Examples are polyvinyl pyrrolidone, polyoxyethylated castor oil, polyoxyethylated sorbitan esters.

Preservatives are: benzyl alcohol, trichlorobutanol, p-hydroxybenzoic acid esters, n-butanol.

Oral solutions are administered directly. Concentrates are administered orally after prior dilution to the administration concentration. Oral solutions and concentrates are prepared as described above in the case of the injection solutions, working under sterile conditions not being necessary.

Solutions for use on the skin are dribbled on, spread on, rubbed in, sprayed on, applied by atomizing or by dipping, bathing or washing. These solutions are prepared as described above in the case of the injection solutions.

The addition of thickeners during the preparation may be advantageous. Thickeners are: inorganic thickeners, such as bentonite, colloidal silica or aluminum monostearate, and organic thickeners, such as cellulose derivatives, polyvinyl alcohols and the copolymers thereof, acrylates and methacrylates.

Gels are applied or sprayed on the skin or inserted in body cavities. Gels are prepared by adding sufficient thickener to solutions which have been prepared as described in the case of the injection solutions, to form a clear mass of ointment-type consistency. The thickeners used are the thickeners indicated further above.

Pour-on formulations are poured or sprayed onto limited areas of the skin, the active compound either penetrating through the skin and acting systemically or being distributed on the body surface.

Pour-on formulations are prepared by dissolving, suspending or emulsifying the active compound in suitable solvents or solvent mixtures which are tolerated by the skin. If required, other auxiliaries, such as colorants, resorption-enhancing substances, antioxidants, agents which bring about protection against the light, or tackifiers can be added.

Solvents which may be mentioned are: water, alkanols, glycols, polyethylene glycols, polypropylene glycols, glycerol, aromatic alcohols, such as benzyl alcohol, phenylethanol or phenoxyethanol, esters, such as ethyl acetate, butyl acetate or benzyl benzoate, ethers, such as alkylene glycol alkyl ethers, such as dipropylene glycol monomethyl ether or diethylene glycol monobutyl ether, ketones, such as acetone or methyl ethyl ketone, aromatic and/or aliphatic hydrocarbons, vegetable or synthetic oils, DMF, dimethylacetamide, N-methyl-pyrrolidone, 2-dimethyl-4-oxy-methylene-1,3-dioxolane.

Colorants are all colorants which are permitted for administration to animals and which can be dissolved or suspended.

Examples of resorption-enhancing substances are DMSO, spreading oils, such as isopropyl myristate, dipropylene glycol pelargonate, silicon oils, fatty acid esters, triglycerides, fatty alcohols.

Antioxidants are sulphites or metabisulphites, such as potassium metabisulphite, ascorbic acid, butylhydroxytoluene, butylhydroxyanisole, tocopherol.

Examples of agents which bring about protection against light are substances from the class of the benzophenones or Novantisol acid.

Examples of tackifiers are cellulose derivatives, starch derivatives, polyacrylates, natural polymers, such as alginates or gelatins.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing the solution with the solvent of the other phase with the aid of suitable emulsifiers and, if appropriate, other auxiliaries, such as colorants, resorption-enhancing substances, preservatives, antioxidants, agents which bring about protection against light or substances which increase the viscosity.

The hydrophobic phase (oils) which may be mentioned are: paraffin oils, silicon oils, natural vegetable oils, such as sesame oil, almond oil, castor oil, synthetic triglycerides, such as caprylic/caprinic acid bigylceride, triglyceride mixture with vegetable fatty acids of chain length $C_{8-12}$ or other specifically selected natural fatty acids, mixtures of partial glycerides of saturated or unsaturated fatty acids which optionally also contain hydroxyl groups, mono- and diglycerides of the $C_8/C_{10}$ fatty acids.

Fatty acid esters, such as ethyl stearate, di-n-butyryl adipate, hexyl laurinate, dipropylene glycol pelargonate, esters of a branched fatty acid of medium chain length with saturated fatty alcohols of chain length $C_{16}-C_{18}$, isopropyl myristate, isopropyl palmitate, capyrlic/caprinic acid esters of saturated fatty alcohols of chain length $C_{12}-C_{18}$, isopropyl stearate, oleyl oleate, decyl oleate, ethyl oleate, ethyl lactate, waxy fatty acid esters, such as dibutyl phthalate, diisopropyl adipate, ester mixtures related to the latter, and other fatty alcohols, such as isotridecyl alcohol, 2-octyldodecanol, cetylstearyl alcohol, oleyl alcohol.

Fatty acids such as, for example, oleic acid and mixtures thereof.

The following may be mentioned as the hydrophilic phase: water, alcohols, such as, for example, propylene glycol, glycerol, sorbitol, and mixtures thereof.

Emulsifiers which may be mentioned are: non-ionic surfactants, for example polyoxyethylated castor oil, polyoxyethylated sorbitan monooleate, sorbitan monostearate, glycerol monostearate, polyoxyethyl stearate, alkylphenol polyglycol ether;

ampholytic surfactants, such as di-Na N-lauryl-$\beta$-iminodipropionate or lecithin;

anion-active surfactants, such as Na lauryl sulphate, fatty alcohol ether sulphates, mono/dialkyl polyglycol ether orthophosphoric acid ester monoethanolamine salt;

cation-active surfactants, such as cetyltrimethylammonium chloride.

Other auxiliaries which may be mentioned are: substances which increase viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, methyl vinyl ether and maleic acid anhydride copolymers, polyethylene glycols, waxes, colloidal silica, or mixtures of the listed substances.

Suspensions can be administered orally, dermally or as an injection. They are prepared by suspending the active compound in an excipient liquid, if appropriate with the addition of further auxiliaries, such as wetting agents, colorants resorption-enhancing substances, preservatives, antioxidant agents which bring about protection from light.

Excipient liquids which may be mentioned are all homogeneous solvents and solvent mixtures.

Wetting agents (dispersing agents) which may be mentioned are the surfactants which are mentioned further above.

Other auxiliaries which may be mentioned are the auxiliaries mentioned further above.

Semi-solid preparations can be administered orally or dermally. From the above-described suspensions and emulsions, they are distinguished only by having a higher viscosity.

For preparing solid preparations, the active compound is mixed with suitable excipients, if appropriate with the addition of auxiliaries, and the mixture is shaped as desired.

Excipients which may be mentioned are all physiologically tolerable, solid inert substances. All these serve inorganic and organic substances. Examples of inorganic substances are common salt, carbonates, such as calcium carbonate, hydrogen carbonates, aluminas, silicas, argillaceous earths, precipitated or colloidal silicon dioxide, phosphates.

Examples of organic substances are sugars, cellulose, foodstuffs and feeds, such as milk powder, animal meals, cereal meals and coarse cereal meals, starches.

Auxiliaries are preservatives, antioxidants or colorants which have already been listed further above.

Other suitable auxiliaries are lubricants and gliding agents, such as, for example, magnesium stearate, stearic acid, talc, bentonites, substances which enhance disintegration, such as starch or crosslinked polyvinylpyrrolidone, binders, such as, for example, starch, gelatin or linear polyvinylpyrrolidone, and also dry binders, such as microcrystalline cellulose.

In the preparations, the active compounds can also be present as a mixture with synergists or with other active compounds.

Ready-for-use preparations contain the active compound in concentrations of 10 ppm–20 per cent by weight, preferably 0.1–10 per cent by weight.

Preparations which are diluted prior to administration contain the active compound in concentrations of 0.5–90 per cent by weight, preferably from 1–50 per cent by weight.

In general, it has proved expedient to administer amounts of approximately 0.5 to approximately 50 mg, preferably 1 to 20 mg, of active compound per kg of body weight per day in order to obtain effective results.

It is also possible to administer the active compounds together with the feed or drinking water of the animals.

Feeds and foodstuffs contain 0.01 to 100 ppm, preferably 0.5 to 50 ppm, of the active compound in combination with a suitable edible material.

Such feed and foodstuff can be used for therapeutic purposes and for prophylactic purposes.

Such feed or foodstuff is prepared by mixing a concentrate or a pre-mix which contains 0.5 to 30%, preferably 1 to 20% by weight, of an active compound in a mixture with an edible organic or inorganic excipient, with customary foodstuffs. Examples of edible excipients are, for example, corn meal or corn plus soy bean meal or mineral salts which preferably contain a small amount of an edible oil for the prevention of dust formation, for example corn oil or soy oil. The pre-mix thus obtained can then be added to the complete foodstuff before it is fed to the animals.

The application in the case of coccidiosis may be mentioned by way of example:

For therapy and prophylaxis of, for example, coccidiosis in birds, in particular in chickens, ducks, geese and turkeys, 0.1 to 100 ppm, preferably 0.5 to 100 ppm, of an active compound are mixed with a suitable edible material, for example a nutritive foodstuff. If desired, it is possible to increase these amounts, in particular when the active compound is well tolerated by the recipient. Accordingly, administration can also be carried out via the drinking water.

For the treatment of individual animals, for example in the case of treatment of coccidiosis in mammals or of toxoplasmosis, it is preferred to administer daily amounts of active compound of 0.5 to 100 mg/kg of body weight in order to achieve the desired results. Nevertheless, it may at times be necessary to deviate from the amounts mentioned, in particular to do so as a function of the body weight of the test animal or of the nature of the administration method, but also because of the species of animal and its individual behavior towards the active compound or the type of formulation and the time or interval over which the administration takes place. Thus, it may be sufficient, in some cases, to manage with less than the abovementioned minimum amount, while in other cases the upper limit mentioned must be exceeded. Where relatively large amounts are administered, it may be advantageous to divide these into several individual administrations over the course of the day.

Fish parasites include, from the subkingdom of the Protozoa, species from the phylum of the Ciliata, for example Ichthyophthirius multifiliis, Chilodonella cyprini, Trichodina spp., Glossatella spp., Epistylis spp., of the phylum of the Myxosporidia, for example Myxosoma cerebralis, Myxidium spp., Myxobolus spp., Heneguya spp., Hoferellus spp., of the class of the Microsporidia, for example Glugea spp., Thelohania spp., Pleistophora spp., from the phylum of the Plathelminthes Trematodes; Monogenea, for example Dactylogyrus spp., Gyrodactylus spp., Pseudodactylogyrus spp., Diplozoon spp., Cestodes, for example from the groups of the Caryphyllidea (for example Caryophyllaeus laticeps), Pseudophyllidea (for example Diphyllobothrium spp.), Tetraphyllidea (for example Phyllobothrium spp.) and Protocephalida (for example species of the genus Proteocephalus) and, from the phylum of the Arthropoda, various parasitic Crustacea, in particular from the subclasses of the Branchiura (fish lice) and Copepoda (copepods) and the orders of the Isopoda (isopods) and Amphipoda (water-fleas).

Treatment of the fish is carried out either orally, for example via the feed or via short-term treatment, "medicinal bath", into which the fish are put and in which they are kept for a certain period (minutes up to several hours), for example when they are transferred from one rearing tank to another.

However, transient or permanent treatment of the environment of the fish (for example of entire pond systems, aquaria, tanks or troughs) in which the fish are kept can also take place.

The active compound is administered in preparations which are designed to suit the applications.

In the preparations, the concentration of the active compound is approximately 1 ppm to 10% by weight.

Preferred preparations for short-term treatment in the administrations as "medicinal bath", for example for the treatment when the fish are transferred or for the treatment of the environment (pond treatment) of the fish are solutions of the active compound in one or more polar solvents which, upon dilution with water, show an alkaline reaction.

For the preparation of these solutions, the active compound is dissolved in a polar, water-soluble solvent which either shows an alkaline reaction or to which an alkaline, water-soluble substance is added. The latter is advantageously likewise dissolved in the solvent, but can also suspended in the solvent to dissolve only upon contact with water. In this case, the water should have a pH of 7-10, but preferably a pH of 8-10, after the active compound solution has been added.

The active compound concentration can be in the range 0.5-50%, but preferably in a range of 1-25%.

Suitable solvents are all water-soluble solvents in which the active compound is soluble in a sufficient concentration and which are physiologically acceptable.

These solvents are ethyl alcohol, isopropyl alcohol, benzyl alcohol, glycerol, propylene glycol, polyethylene glycols, poly(oxoethylene)/poly(oxypropylene) polymers, basic alcohols, such as mono-, di- and triethanolamine, ketones, such as acetone or methyl ethyl ketone, esters, such as ethyl lactate, furthermore N-methylpyrrolidone, dimethylacetamide, dimethylformamide, furthermore dispersing and emulsifying agents, such as polyoxyethylated castor oil, polyethylene glycol sorbitan monooleate, polyethylene glycol stearate, or polyethylene glycol ether, polyethylene glycol alkylamines.

Bases which may be mentioned for adjusting the alkaline pH are organic bases such as basic amino acids, such as L- or D,L-arginine, L- or D,L-lysine, methylglucosamine, glucosamine,2-amino-2-hydroxymethylpropane(1,3)-diol, such as, furthermore, N,N,N',N'-tetrakis-(2-hydroxypropyl)-ethylenediamine or polyether tetrol on the basis of ethylenediamine (M.W. 480–420), inorganic bases, such as ammonia or sodium carbonate, if appropriate with the addition of water.

The preparations can also contain 0.1 to 20% by weight, preferably 0.1-10% by weight, of other formulation auxiliaries, such as antioxidants, surfactants, suspension stabilizers and thickeners, such as, for example, methylcellulose, alginates, polysaccharides, galactomannans and colloidal silica. It is also possible to add colourants, flavour and nutrient components for animal feeding. Acids which form a buffer system with the initially introduced base or which reduce the pH of the solution may also be mentioned in this context.

The active compound concentration for administration depends on the type and duration of the treatment and on the age and condition of the treated fish. For example, for short-term treatment, it is 2-50 mg of active compound per liter of water, preferably 5-10 mg per liter, at a treatment period of 3-4 hours. For example, young carp are treated at a concentration of 5-10 mg/l and for a treatment period of approximately 1-4 hours.

Eels are treated with concentrations of approximately 5 mg/l for approximately 4 hours.

A correspondingly lower concentration is chosen when the treatment period is longer or when permanent treatment is carried out.

For pond treatments, 0.1-5 mg of active compound can be used per liter of water.

Preparations for administration as feed additive may have the following composition:

| a) | Active compound of the formula I | 1-10 parts by wt. |
|---|---|---|
|  | Soy - bean protein | 49-90 parts by wt. |
| b) | Active compound of the formula I | 0.5-10 parts by wt. |
|  | Benzyl alcohol | 0.08-1.4 parts by wt. |
|  | Hydroxypropylmethyl cellulose | 0-3.5 parts by wt. |
|  | Water | Remainder to 100 |

Preparations for administration as "medicinal baths" and for pond treatment may have the following composition and may be prepared as follows:

c) 2.5 g of active compound of the formula (I) are dissolved in 100 ml of triethanolamine with heating.

d) 2.5 g of active compound of the formula (I), 12.5 g of lactic acid are dissolved in 100 ml of triethanolamine with heating and stirring.

e) 10.0 g of active compound of the formula (I) are dissolved in 100 ml of monoethanolamine.

| f) | Active compound of the formula I | 5.0 g |
|---|---|---|
|  | Propylene glycol | 50.0 g |
|  | Sodium carbonate | 5.0 g |
|  | Water | to 100 ml |
| g) | Active compound of the formula I | 5.0 g |
|  | Monoethanolamine | 10 g |
|  | N-Methylpyrrolidone | to 100 ml |
| h) | Active compound of the formula I | 2.5 g |
|  | Sodium carbonate | 5.0 g |
|  | Polyethylene glycol 200 | to 100 ml |

The active compound is dissolved in polyethylene glycol with heating, and sodium carbonate is suspended in the solution.

EXAMPLE A

Coccidiosis in Chickens

Chickens of age 9 to 11 days were infected with 40,000 sporulated oocysts of highly virulent strains of Eiveria acervulina, E. maxima and E. tenella, the pathogens of intestinal coccidiosis.

3 days prior to infection and 8 days after the infection (end of experiment), active compound was administered in the concentration indicated by admixing it to the feed of the animals.

The number of oocysts in the faeces was determined with the aid of the McMaster chamber (see Engelbrecht and coworkers, "Parasitologische Arbeitsmehoden in Medizin und Veterinärmedizin [Parasitological Methods in Medicine and Veterinary Medicine]", p. 172, Akademie Verlag, Berlin (1965)).

Doses which were considered as effective were those which prevented the excretion of oocysts and/or clinical coccidiosis symptoms including mortality, either completely or to a large extent. The effective doses are indicated in the table which follows.

TABLE 1

Coccidiosis in chickens

| Example No. | Doses ppm | Mortality dead/ initial number | Excretion of oocysts as % in comparison with the untreated infected control | Gain in weight as % compared with the non-infected untreated control | Excretion of blood with the faeces |
|---|---|---|---|---|---|
| untreated infected control |  | 2/6 | 100 | 35 | copious |
| 1 | 50 | 0/3 | 0 | 100 | none |

PREPARATION EXAMPLES

I Examples of Process 2a

Example 1

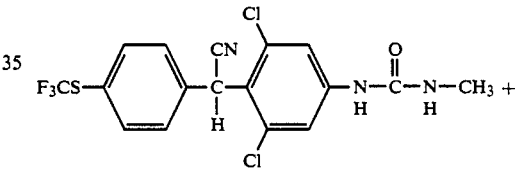

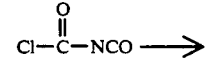

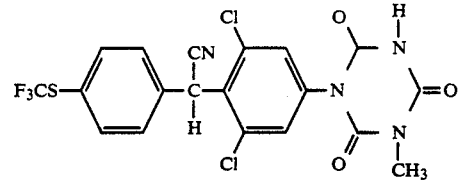

8 g (0.027 mol) of 2,6-dichloro-α-(4-trifluoromethylthiophenyl)-4-methylureido-phenylacetonitrile are suspended in 130 ml of dry toluene, and 3.6 g (0.035 mol) of chlorocarbonyl isocyanate are added. The mixture is stirred for 3 hours at 60° C. and allowed to cool, and any precipitated product is filtered off with suction and washed thoroughly with cyclohexane. In this way, 8.5 g (91% of theory) of the triazinetrione are obtained.

The following are prepared analogously:

Example 2

2,6-Dichloro-α-(4-chlorophenyl)-4-(3N-methyl-1,3,5-triazine-2,4,6-(1H,3H,5H)-trione)-phenylacetonitrile

Example 3

2,6-Dichloro-α-(3,4-dichlorophenyl)-4-(3N-methyl-1,3,5-triazine-2,4,6-(1H,3H,5H)-trione)-phenylacetonitrile

Example 4

2,6-Dichloro-α-(4-trifluoromethylthiophenyl)-4-(3N-methyl-1,3,5-triazine-2,4,6-(1H,3H,5H)-trione)-phenylacetontrile

II Example of Process 2b

Example 5

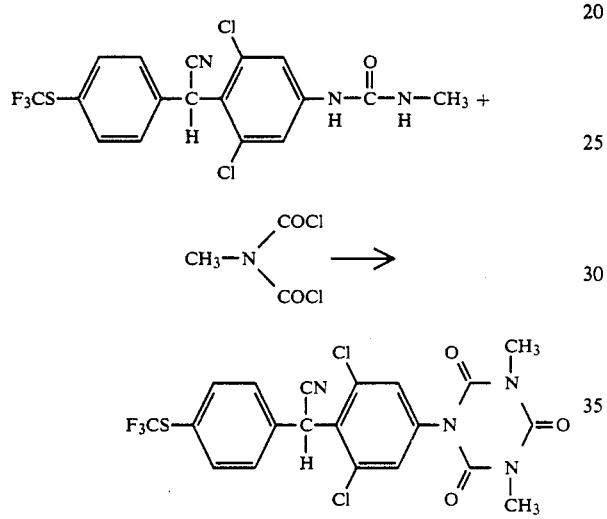

7.4 g (0.017 mol) of 2,6-dichloro-α-(4-trifluoromethylthiophenyl)-4-methylureido-phenylacetonitrile are suspended in 100 ml of chlorobenzene. 2.8 g (0.018 mol) of bischlorocarbonylamine in 20 ml of chlorobenzene are added dropwise to the suspension. The mixture is heated to 110° C. and stirred for 3 hours at this temperature. The mixture is allowed to cool, and the solid is filtered off with suction and washed with cyclohexane. In this way, 5.9 g (67% of theory) of the triazinetrione are obtained.

III Example of Process 2c

Example 6

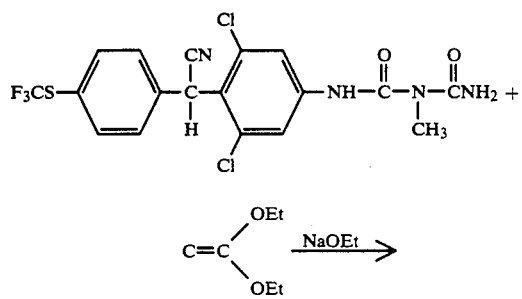

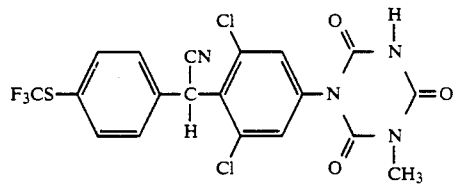

6.3 g (0.014 mol) of 2,6-dichloro-α-(4-trifluoromethylthiophenyl)-4-methylbisureido-phenylacetonitrile are suspended in 20 ml of diethyl carbonate, and the suspension is stirred for 4 hours at 20° C. When the reaction is complete, water is added and the mixture is rendered neutral using dilute HCl. The reaction mixture is concentrated, and any precipitated solid is filtered off with suction. In this way, 5.8 g (85% of theory) of the triazinetrione are obtained.

IV Example of Process 2d

Example 7

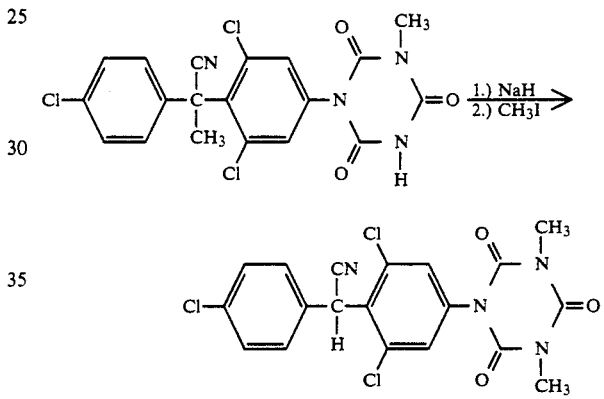

4 g (9.2 mmol) of 2,6-Dichloro-α-(4-chlorophenyl)-α-methyl-4-(3-N-methyl-1,3,5-triazine-2,4,6-(1H,3H,5H)-trione)-phenylacetonitrile are dissolved in 20 ml of absolute DMSO, and 0.21 g of sodium hydride are added to the solution. The mixture is stirred for 30 minutes at room temperature, and 2 g (14 mmol) of methyl iodide in 5 ml of DMSO are then added under argon. The mixture is warmed to 50° C. and maintained at this temperature for 4 hours. The reaction mixture is subsequently concentrated in vacuo, and water is then added. The product is filtered off with suction, and 3 (73%) of the N,N'-dimethyl compound are obtained in this way.

V Example of Process 4a

Example Va

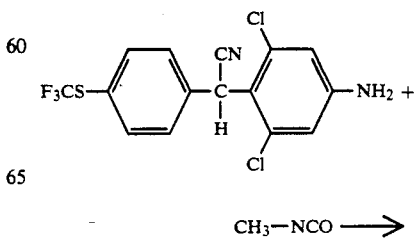

CH₃—NCO ⟶

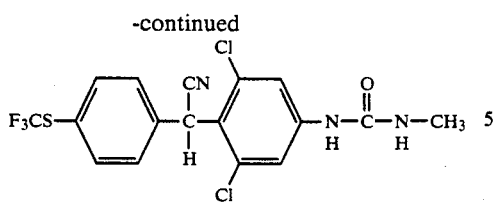

10 g (0.027 mol) of 4-amino-2,6-dichloro-α-(4-trifluoromethylthiophenyl)-phenylacetonitrile are dissolved in 120 ml of dry pyridine. 2 g (0.035 mol) of methyl isocyanate are added dropwise to this solution, and stirring is continued for 15 hours at 30° C. Water is added slowly to the reaction mixture, and the precipitated solid is filtered off. In this way, 10.2 g (88% of theory) of the methylurea are obtained.

The following are prepared analogously:

Example Vb
2,6-Dichloro-α-(4-trifluoromethoxyphenyl)-4-methylureidophenylacetonitrile

Example Vc
2,6-Dichloro-α-(4-chlorophenyl)-4-methylureido-phenylacetonitrile

VI Example of Process 4b

Example VIa

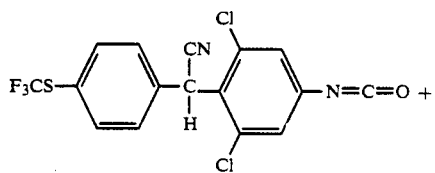

C₃H₇NH₂ ⟶

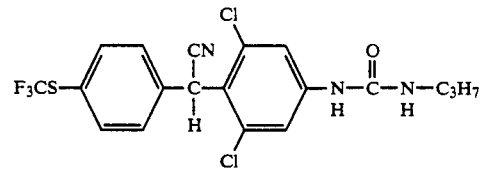

3.5 g (8.1 mmol) of 4-isocyanato-2,6-dichloro-α-(4-trifluoromethylthiophenyl)-phenylacetonitrile are dissolved in 30 ml of absolute toluene under argon, and a solution of 0.6 g (10 mmol) of propylamine in 20 ml of toluene is added at room temperature to the solution. The mixture is heated for 1 hour at 60° C., and then for 2 hours at 90° C. After the volatile constituents have been stripped off in vacuo and after the residue has been recrystallized from ethanol, 2.4 g (64% of theory) of the propylurea are obtained.

VII Example of Process 6

Example VIIa

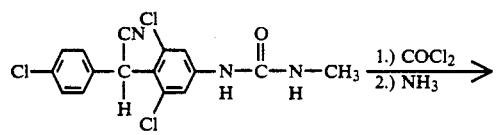

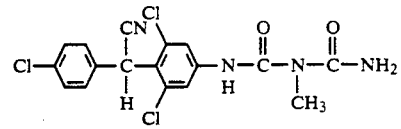

12 g of 20% strength (0.025 mol) of toluenic phosgene solution are added at room temperature to 5 g (0.014 mol) of 2,6-dichloro-α-(4-chlorophenyl)-4-methylureido-phenylacetonitrile in 70 ml of dry toluene. Stirring is continued at room temperature for 10 hours, and the mixture is subsequently heated at 60° C. for 4 hours. After the reaction mixture has cooled down, ammonia is passed through at room temperature until reaction of the phosgene adduct is complete. When the reaction is complete, the precipitated solid is filtered off. In this way, 4.1 g (72% of theory) of the biuret are obtained.

The following are prepared analogously:

Example VIIb
2,6-Dichloro-α-(trifluoromethylthiophenyl)-4-N,-methylbisureido-phenylacetonitrile

Example VIIC
2,6-Dichloro-α-(trifluoromethoxyphenyl)-4-N,-methyl-bisureido-phenylacetonitrile

VIII Example of Process 8

Example VIIIa

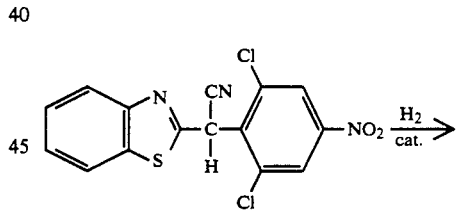

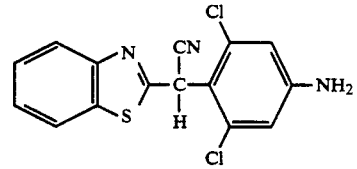

20 g (0.055 mol) of 4-nitro-2,6-dichloro-α-(2-benzothiazolyl)-phenylacetonitrile are dissolved in 100 ml of dioxane and 100 ml of ethanol and hydrogenated under atmospheric pressure and at room temperature with the addition of 4 g of Pd (10% on activated charcoal). After the catalyst has been filtered off and the solvent has been stripped off, 16.9 (92% of theory) of the amine are obtained.

The following are prepared analogously:

Example VIIIb

4-Amino-2,6-dichloro-α-(2-pyridinyl)-phenyl-acetonitrile

Example VIIIc

4-Amino-2,6-dichloro-=-(3-pyridinyl)-phenyl-acetonitrile

IX Example of Process 10

Example IXa

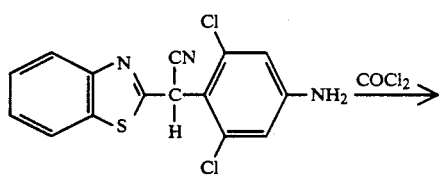

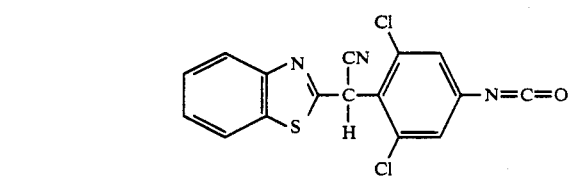

4 g (0.012 mol) of 2,6-dichloro-α-(2-benzothiazolyl)-4-aminophenylacetonitrile, dissolved in 50 ml of toluene, are added dropwise to 7.8 g (0.016 mol) of phosgene in toluene. When the dropwise addition is complete, the mixture is slowly heated to room temperature, stirred at room temperature for 1 hour and then heated slowly to the boil in the course of one further hour. The mixture is stirred under reflux for 2 more hours and cooled, and the volatile constituents are distilled off in vacuo and the residue is digested with a little diethyl ether. In this way, 3.7 g (85% of theory) of theisocyanate are obtained as a solid.

X Example of Process 12

Example Xa

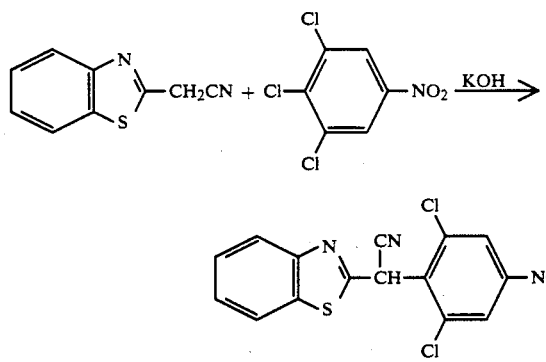

17.4 g (0.1 mol) of 2-benzothiazolylacetonitrile, 2.6 g (0.1 mol) of 3,4,5-trichloronitrobenzene and 5.6 g (0.1 mol) of KOH are refluxed for 12 hours in 500 ml of acetonitrile. The mixture is subsequently cooled, diluted with water and acidified using HCl. The precipitated solid is filtered off. In this way, 26.9 g (74% of theory) of the nitro compound are obtained.

The following are prepared analogously:

Example Xb

4-Nitro-2,6-dichloro-α-(2-pyridinyl)-phenylacetonitrile

Example Xc

4-Nitro-2,6-dichloro-α-(3-pyridinyl)-phenylacetonitrile

It is understood that the specification and examples are illustrative but not limitative of the present invention and that other embodiments within the spirit and scope of the invention will suggest themselves to those skilled in the art.

We claim:

1. A compound of the formula

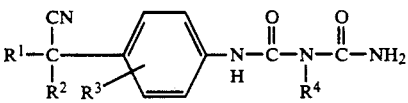

in which $R^1$ represents phenyl or naphthyl, each of which is optionally substituted by halogen, alkyl, cyano, nitro, alkoxy, alkylthio, halogenalkyl, halogenoalkoxy, halogenalkylthio, halogenoalkylsulphinyl or halogenoalkylsulphonyl, $R^2$ represents H, alkyl, alkenyl, alkinyl or aralkyl, $R^3$ represents one or more identical or different radicals from the group consisting of hydrogen, halogen, alkyl, halogenoalkyl, alkoxy, alkylthio, halogenoalkoxy, halogenoalkylthio, cyano, alkoxycarbonyl, alkylsulphonyl and halogenoalkylsulphonyl, and $R^4$ represents hydrogen, alkyl, alkenyl or alkinyl, each of which is optionally substituted by halogen, halogenoalkyl, alkoxy, alkylthio, phenoxy, phenylthio or phenyl, the alkyl, alkenyl and alkinyl moieties having 4 carbon atoms.

2. A compound according to claim 1, in which $R^1$ represents phenyl which is substituted by one or more identical or different radicals from the group consisting of halogen, $C_{1-4}$-alkyl, $C_{1-4}$-halogenoalkyl, $C_{1-4}$-alkoxy, $C_{1-4}$-alkylthio, $C_{1-4}$-halogenoalkoxy, $C_{1-4}$-halogenoalkylthio, cyano, $C_{1-4}$-alkoxycarbonyl, $C_{1-4}$-alkylsulphinyl, $C_{1-4}$-alkylsulphonyl, $C_{1-4}$-halogenoalkylsulphinyl and $C_{1-4}$-halogenoalkylsulphonyl, $R^2$ represents hydrogen or alkyl, $R^3$ represents one or more identical or different radicals from the group consisting of hydrogen, halogen, alkyl, halogenoalkyl, alkoxy, alkylthio, halogenoalkoxy, halogenoalkylthio, cyano, alkoxycarbonyl, alkylsulphonyl and halogenoalkylsulphonyl, and $R^4$ represents hydrogen, alkyl, alkenyl or alkinyl, each of which is optionally substituted by halogen, halogenoalkyl, alkoxy, alkylthio, aryloxy, arylthio or phenyl.

* * * * *

UNITED STATES PATENT AND TRADEMARK OFFICE
CERTIFICATE OF CORRECTION

PATENT NO. : 5,196,562

DATED : March 23, 1993

INVENTOR(S) : Lindner, et al.

It is certified that error appears in the above-identified patent and that said Letters Patent is hereby corrected as shown below:

Col. 30, line 25    After " represents " insert -- benzothi-azolyl --

Col. 30, line 41    After " having " insert -- up to --

Signed and Sealed this

Twentieth Day of September, 1994

Attest:

BRUCE LEHMAN

Attesting Officer    Commissioner of Patents and Trademarks